(12) United States Patent
Williams et al.

(10) Patent No.: US 7,037,687 B2
(45) Date of Patent: May 2, 2006

(54) METHOD OF DETERMINING THE NUCLEOTIDE SEQUENCE OF OLIGONUCLEOTIDES AND DNA MOLECULES

(75) Inventors: Peter Williams, Phoenix, AZ (US); Mark A. Hayes, Chandler, AZ (US); Seth D. Rose, Tempe, AZ (US); Linda B. Bloom, Chandler, AZ (US); Linda J. Reha-Krantz, Edmonton (CA); Vincent B. Pizziconi, Phoenix, AZ (US)

(73) Assignees: Arizona Board of Regents, Tempe, AZ (US); University of Alberta, Edmonton, Alberta (CA)

( * ) Notice: Subject to any disclaimer, the term of this patent is extended or adjusted under 35 U.S.C. 154(b) by 424 days.

(21) Appl. No.: 10/229,997

(22) Filed: Aug. 28, 2002

(65) Prior Publication Data

US 2003/0138809 A1    Jul. 24, 2003

Related U.S. Application Data

(63) Continuation of application No. 09/673,544, filed as application No. PCT/US99/09616 on Apr. 30, 1999, now abandoned.

(60) Provisional application No. 60/083,840, filed on May 1, 1998.

(51) Int. Cl.
*C12P 19/34* (2006.01)
*C12Q 1/68* (2006.01)
*C07H 21/00* (2006.01)

(52) U.S. Cl. .................... 435/91.1; 435/6; 435/91.2; 536/22.1; 536/23.1

(58) Field of Classification Search ............. 435/6, 435/91.1, 91.2; 536/22.1, 23.1
See application file for complete search history.

(56) References Cited

U.S. PATENT DOCUMENTS

| 5,302,509 A | | 4/1994 | Cheeseman |
| 5,436,149 A | * | 7/1995 | Barnes .................. 435/194 |
| 5,547,859 A | | 8/1996 | Goodman et al. |
| 5,945,284 A | | 8/1999 | Livak et al. |
| 6,028,190 A | | 2/2000 | Mathies et al. |
| 6,087,095 A | | 7/2000 | Rosenthal et al. |

FOREIGN PATENT DOCUMENTS

| EP | 0 223 618 | 5/1987 |
| WO | WO 89/09283 | 10/1989 |
| WO | WO 90/13666 | 11/1990 |
| WO | WO 91/06678 | 5/1991 |
| WO | 96/27025 | 8/1996 |

* cited by examiner

*Primary Examiner*—Jezia Riley
(74) *Attorney, Agent, or Firm*—Thomas C. Meyers; Proskauer Rose LLP

(57) ABSTRACT

The present invention relates to a novel method for analyzing nucleic acid sequences based on real-time detection of DNA polymerase-catalyzed incorporation of each of the four nucleotide bases, supplied individually and serially in a microfluidic system, to a reaction cell containing a template system comprising a DNA fragment of unknown sequence and an oligonucleotide primer. Incorporation of a nucleotide base into the template system can be detected by any of a variety of methods including but not limited to fluorescence and chemiluminescence detection. Alternatively, microcalorimetic detection of the heat generated by the incorporation of a nucleotide into the extending template system using thermopile, thermistor and refractive index measurements can be used to detect extension reactions.

5 Claims, 9 Drawing Sheets

METHOD OF DETERMINING THE NUCLEOTIDE SEQUENCE OF OLIGONUCLEOTIDES AND DNA MOLECULES

REFERENCE TO RELATED APPLICATIONS

This application is a continuation of U.S. application Ser. No. 09/673,544, filed on Feb. 26, 2001, now abandoned, which is a national stage filing of International Application No. PCT/US99/09616, filed on Apr. 30, 1999, which claimed the benefit of U.S. Provisional Application No. 60/083,840, filed on May 1, 1998, each of the foregoing of which is incorporated by reference herein.

The present invention relates to a novel method for analyzing nucleic acid sequences based on real-time detection of DNA polymerase-catalyzed incorporation of each of the four deoxynucleoside monophosphates, supplied individually and serially as deoxynucleoside triphosphates in a microfluidic system, to a template system comprising a DNA fragment of unknown sequence and an oligonucleotide primer. Incorporation of a deoxynucleoside monophosphate (dNMP) into the primer can be detected by any of a variety of methods including but not limited to fluorescence and chemiluminescence detection. Alternatively, microcalorimetic detection of the heat generated by the incorporation of a dNMP into the extending primer using thermopile, thermistor and refractive index measurements can be used to detect extension reactions.

The present invention provides a method for sequencing DNA that avoids electrophoretic separation of DNA fragments thus eliminating the problems associated with anomalous migration of DNA due to repeated base sequences or other self-complementary sequences which can cause single-stranded DNA to self-hybridize into hairpin loops, and also avoids current limitations on the size of fragments that can be read. The method of the invention can be utilized to determine the nucleotide sequence of genomic or cDNA fragments, or alternatively, as a diagnostic tool for sequencing patient derived DNA samples.

BACKGROUND OF THE INVENTION

Currently, two approaches are utilized for DNA sequence determination: the dideoxy chain termination method of Sanger (1977, Proc. Natl. Acad. Sci. 74:5463–5674) and the chemical degradation method of Maxam (1977, Proc. Natl. Acad. Sci. 74:560–564). The Sanger dideoxy chain termination method is the most widely used method and is the method upon which automated DNA sequencing machines rely. In the chain termination method, DNA polymerase enzyme is added to four separate reaction systems to make multiple copies of a template DNA strand in which the growth process has been arrested at each occurrence of an A, in one set of reactions, and a G, C, or T, respectively, in the other sets of reactions, by incorporating in each reaction system one nucleotide type lacking the 3'-OH on the deoxyribose at which chain extension occurs. This procedure produces a series of DNA fragments of different lengths, and it is the length of the extended DNA fragment that signals the position along the template strand at which each of four bases occur. To determine the nucleotide sequence, the DNA fragments are separated by high resolution gel electrophoresis and the order of the four bases is read from the gel.

A major research goal is to derive the DNA sequence of the entire human genome. To meet this goal the need has developed for new genomic sequencing technology that can dispense with the difficulties of gel electrophoresis, lower the costs of performing sequencing reactions, including reagent costs, increase the speed and accuracy of sequencing, and increase the length of sequence that can be read in a single step. Potential improvements in sequencing speed may be provided by a commercialized capillary gel electrophoresis technique such as that described in Marshall and Pennisis (1998, Science 280:994–995). However, a major problem common to all gel electrophoresis approaches is the occurrence of DNA sequence compressions, usually arising from secondary structures in the DNA fragment, which result in anomalous migration of certain DNA fragments through the gel.

As genomic information accumulates and the relationships between gene mutations and specific diseases are identified, there will be a growing need for diagnostic methods for identification of mutations. In contrast to the large scale methods needed for sequencing large segments of the human genome, what is needed for diagnostic methods are repetitive, low-cost, highly accurate techniques for resequencing of certain small isolated regions of the genome. In such instances, methods of sequencing based on gel electrophoresis readout become far too slow and expensive.

When considering novel DNA sequencing techniques, the possibility of reading the sequence directly, much as the cell does, rather than indirectly as in the Sanger dideoxynucleotide approach, is a preferred goal. This was the goal of early unsuccessful attempts to determine the shapes of the individual nucleotide bases with scanning probe microscopes.

Additionally, another approach for reading a nucleotide sequence directly is to treat the DNA with an exonuclease coupled with a detection scheme for identifying each nucleotide sequentially released as described in Goodwin et al., (1995, Experimental Techniques of Physics 41:279–294). However, researchers using this technology are confronted with the enormous problem of detecting and identifying single nucleotide molecules as they are digested from a single DNA strand. Simultaneous exonuclease digestion of multiple DNA strands to yield larger signals is not feasible because the enzymes rapidly get out of phase, so that nucleotides from different positions on the different strands are released together, and the sequences become unreadable. It would be highly beneficial if some means of external regulation of the exonuclease could be found so that multiple enzyme molecules could be compelled to operate in phase. However, external regulation of an enzyme that remains docked to its polymeric substrate is exceptionally difficult, if not impossible, because after each digestion the next substrate segment is immediately present at the active site. Thus, any controlling signal must be present at the active site at the start of each reaction.

A variety of methods may be used to detect the polymerase-catalyzed incorporation of deoxynucleoside monophosphates (dNMPs) into a primer at each template site. For example, the pyrophosphate released whenever DNA polymerase adds one of the four dNTPs onto a primer 3' end may be detected using a chemiluminescent based detection of the pyrophosphate as described in Hyman E. D. (1988, Analytical Biochemistry 174:423–436) and U.S. Pat. No. 4,971,903. This approach has been utilized most recently in a sequencing approach referred to as "sequencing by incorporation" as described in Ronaghi (1996, Analytical Biochem. 242:84) and Ronaghi (1998, Science 281:363–365). However, there exist two key problems associated with this approach, destruction of unincorporated nucleotides and detection of pyrophosphate. The solution to the first problem is to destroy the added, unincorporated nucleotides using a dNTP-digesting enzyme such as apyrase. The solution to the second is the detection of the pyrophosphate using ATP sulfurylase to reconvert the pyrophosphate to ATP which can be detected by a luciferase chemiluminescent reaction as described in U.S. Pat. No. 4,971,903 and Ronaghi (1998, Science 281:363–365). Deoxyadenosine α-thiotriphosphate is used instead of dATP to minimize direct interaction of injected dATP with the luciferase.

Unfortunately, the requirement for multiple enzyme reactions to be completed in each cycle imposes restrictions on the speed of this approach while the read length is limited by the impossibility of completely destroying unincorporated, non-complementary, nucleotides. If some residual amount of one nucleotide remains in the reaction system at the time when a fresh aliquot of a different nucleotide is added for the next extension reaction, there exists a possibility that some fraction of the primer strands will be extended by two or more nucleotides, the added nucleotide type and the residual impurity type, if these match the template sequence, and so this fraction of the primer strands will then be out of phase with the remainder. This out of phase component produces an erroneous incorporation signal which grows larger with each cycle and ultimately makes the sequence unreadable.

A different direct sequencing approach uses dNTPs tagged at the 3' OH position with four different colored fluorescent tags, one for each of the four nucleotides is described in Metzger, M. L., et al. (1994, Nucleic Acids Research 22:4259–4267). In this approach, the primer/template duplex is contacted with all four dNTPs simultaneously. Incorporation of a 3' tagged NMP blocks further chain extension. The excess and unreacted dNTPs are flushed away and the incorporated nucleotide is identified by the color of the incorporated fluorescent tag. The fluorescent tag must then be removed in order for a subsequent incorporation reaction to occur. Similar to the pyrophosphate detection method, incomplete removal of a blocking fluorescent tag leaves some primer strands unextended on the next reaction cycle, and if these are subsequently unblocked in a later cycle, once again an out-of-phase signal is produced which grows larger with each cycle and ultimately limits the read length. To date, this method has so far been demonstrated to work for only a single base extension. Thus, this method is slow and is likely to be restricted to very short read lengths due to the fact that 99% efficiency in removal of the tag is required to read beyond 50 base pairs. Incomplete removal of the label results in out of phase extended DNA strands.

SUMMARY OF THE INVENTION

Accordingly, it is an object of the present invention to provide a novel method for determining the nucleotide sequence of a DNA fragment which eliminates the need for electrophoretic separation of DNA fragments. The inventive method, referred to herein as "reactive sequencing", is based on detection of DNA polymerase catalyzed incorporation of each of the four nucleotide types, when deoxynucleoside triphosphates (dNTP's) are supplied individually and serially to a DNA primer/template system. The DNA primer/template system comprises a single stranded DNA fragment of unknown sequence, an oligonucleotide primer that forms a matched duplex with a short region of the single stranded DNA, and a DNA polymerase enzyme. The enzyme may either be already present in the template system, or may be supplied together with the dNTP solution.

Typically a single deoxynucleoside triphosphate (dNTP) is added to the DNA primer template system and allowed to react. As used herein deoxyribonucleotide means and includes, in addition to dGTP, dCTP, dATP, dTTP, chemically modified versions of these deoxyribonucleotides or analogs thereof. Such chemically modified deoxyribonucleotides include but are not limited to those deoxyribonucleotides tagged with a fluorescent or chemiluminescent moiety. Analogs of deoxyribonucleotides that may be used include but are not limited to 7-deazapurine. An extension reaction will occur only when the incoming dNTP base is complementary to the next unpaired base of the DNA template beyond the 3' end of the primer. While the reaction is occurring, or after a delay of sufficient duration to allow a reaction to occur, the system is tested to determine whether an additional nucleotide derived from the added dNTP has been incorporated into the DNA primer/template system. A correlation between the dNTP added to the reaction cell and detection of an incorporation signal identifies the nucleotide incorporated into the primer/template. The amplitude of the incorporation signal identifies the number of nucleotides incorporated, and thereby quantifies single base repeat lengths where these occur. By repeating this process with each of the four nucleotides individually, the sequence of the template can be directly read in the 5' to 3' direction one nucleotide at a time.

Detection of the polymerase mediated extension reaction and quantification of the extent of reaction can occur by a variety of different techniques, including but not limited to, microcalorimetic detection of the heat generated by the incorporation of a nucleotide into the extending duplex. Optical detection of an extension reaction by fluorescence or chemiluminescence may also be used to detect incorporation of nucleotides tagged with fluorescent or chemiluminescent entities into the extending duplex. Where the incorporated nucleotide is tagged with a fluorophore, excess unincorporated nucleotide is removed, and the template system is illuminated to stimulate fluorescence from the incorporated nucleotide. The fluorescent tag must then be cleaved and removed from the DNA template system before a subsequent incorporation cycle begins. A similar process is followed for chemiluminescent tags, with the chemiluminescent reaction being stimulated by introducing an appropriate reagent into the system, again after excess unreacted tagged dNTP has been removed; however, chemiluminescent tags are typically destroyed in the process of readout and so a separate cleavage and removal step following detection may not be required. For either type of tag, fluorescent or chemiluminescent, the tag may also be cleaved after incorporation and transported to a separate detection chamber for fluorescent or chemiluminescent detection. In this way, fluorescent quenching by adjacent fluorophore tags incorporated in a single base repeat sequence may be avoided. In addition, this may protect the DNA template system from possible radiation damage in the case of fluorescent detection or from possible chemical damage in the case of chemiluminescent detection.

The present invention further provides a reactive sequencing method that utilizes a two cycle system. An exonuclease-deficient polymerase is used in the first cycle and a mixture of exonuclease-deficient and exonuclease-proficient enzymes are used in the second cycle. In the first cycle, the template-primer system together with an exonuclease-deficient polymerase will be presented sequentially with each of the four possible nucleotides. In the second cycle, after identification of the correct nucleotide, a mixture of exonuclease proficient and deficient polymerases, or a polymerase containing both types of activity will be added in a second cycle together with the correct dNTP identified in the first cycle to complete and proofread the primer extension. In this way, an exonuclease-proficient polymerase is only present in the reaction cell when the correct dNTP is present, so that exonucleolytic degradation of correctly extended strands does not occur, while degradation and correct re-extension of previously incorrectly extended strands does occur, thus achieving extremely accurate strand extension.

The present invention further provides an apparatus for DNA sequencing comprising: (a) at least one chamber including a DNA primer/template system which produces a detectable signal when a DNA polymerase enzyme incorporates a deoxyribonucleotide monophosphate onto the 3' end of the primer strand; (b) means for introducing into, and evacuating from, the reaction chamber at least one selected from the group consisting of buffers, electrolytes, DNA template, DNA primer, deoxyribonucleotides, and polymerase enzymes; (c) means for amplifying said signal; and (d) means for converting said signal into an electrical signal.

BRIEF DESCRIPTION OF THE DRAWINGS

Further objects and advantages of the invention will be apparent from a reading of the following description in conjunction with the accompanying drawings, in which.

DETAILED DESCRIPTION OF THE PREFERRED EMBODIMENTS

Figure 1:
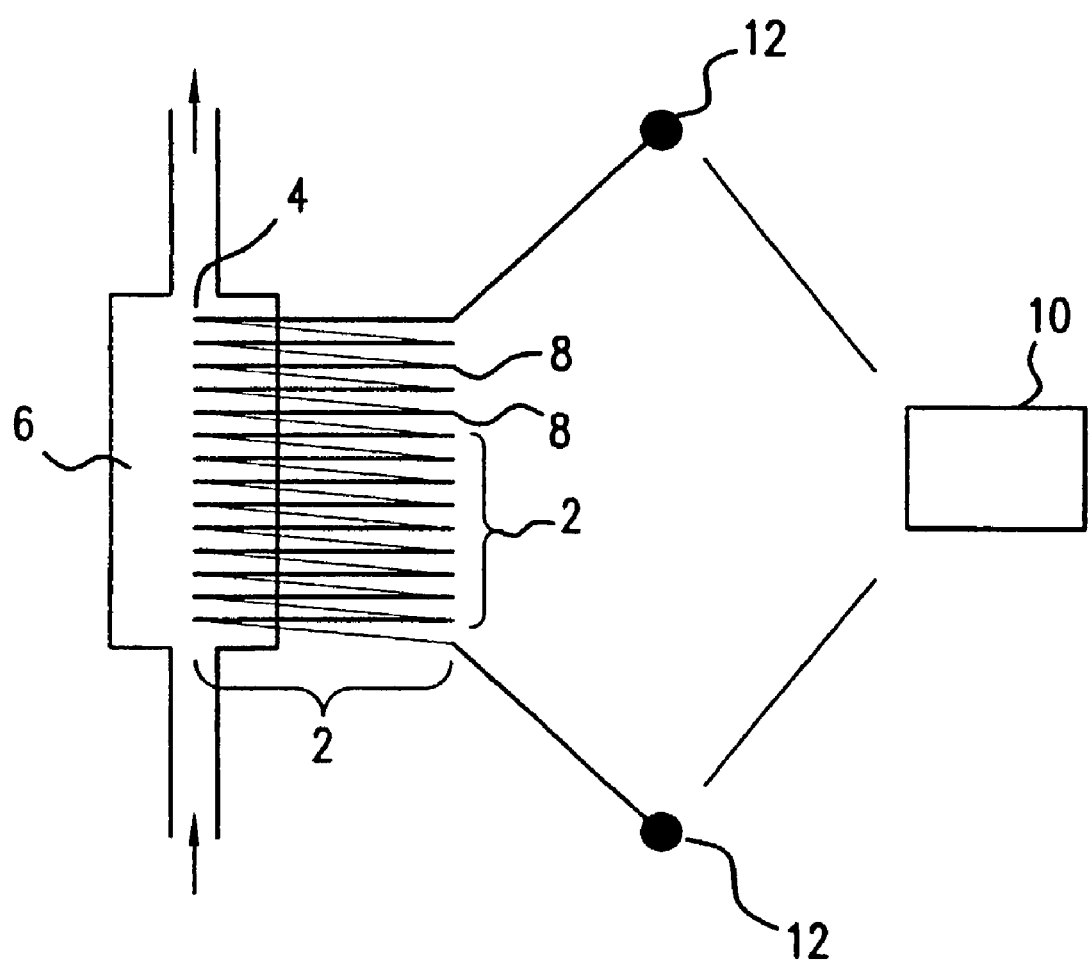
FIG. 1 is a schematic diagram illustrating a reactive sequencing device containing a thin film bismuth antimony thermopile in accordance with the invention.

The present invention provides a method for determining the nucleic acid sequence of a DNA molecule based on detection of successive single nucleotide DNA polymerase mediated extension reactions. As described in detail below, in one embodiment, a DNA primer/template system comprising a polynucleotide primer complementary to and bound to a region of the DNA to be sequenced is constrained within a reaction cell into which buffer solutions containing various reagents necessary for a DNA polymerase reaction to occur are added. Into the reaction cell, a single type of deoxynucleoside triphosphate (dNTP) is added. Depending on the identity of the next complementary site in the DNA primer/template system, an extension reaction will occur only when the appropriate nucleotide is present in the reaction cell. A correlation between the nucleotide present in the reaction cell and detection of an incorporation signal identifies the next nucleotide of the template. Following each extension reaction, the reaction cell is flushed with dNTP-free buffer, retaining the DNA primer/template system, and the cycle is repeated until the entire nucleotide sequence is identified.

The present invention is based on the existence of a control signal within the active site of DNA polymerases which distinguish, with high fidelity, complementary and non-complementary fits of incoming deoxynucleotide triphosphates to the base on the template strand at the primer extension site, i.e., to read the sequence, and to incorporate at that site only the one type of deoxynucleotide that is complementary. That is, if the available nucleotide type is not complementary to the next template site, the polymerase is inactive, thus, the template sequence is the DNA polymerase control signal. Therefore, by contacting a DNA polymerase system with a single nucleotide type rather than all four, the next base in the sequence can be identified by detecting whether of not a reaction occurs. Further, single base repeat lengths can be quantified by quantifying the extent of reaction.

As a first step in the practice of the inventive method, single-stranded template DNA to be sequenced is prepared using any of a variety of different methods known in the art. Two types of DNA can be used as templates in the sequencing reactions. Pure single-stranded DNA such as that obtained from recombinant bacteriophage can be used. The use of bacteriophage provides a method for producing large quantities of pure single stranded template. Alternatively, single-stranded DNA may be derived from double-stranded DNA that has been denatured by heat or alkaline conditions, as described in Chen and Subrung, (1985, DNA 4:165); Huttoi and Skaki (1986, Anal. Biochem. 152:232); and Mierendorf and Pfeffer, (1987, Methods Enzymol. 152:556), may be used. Such double stranded DNA includes, for example, DNA samples derived from patients to be used in diagnostic sequencing reactions.

The template DNA can be prepared by various techniques well known to those of skill in the art. For example, template DNA can be prepared as vector inserts using any conventional cloning methods, including those used frequently for sequencing. Such methods can be found in Sambrook et al., Molecular Cloning: A Laboratory Manual, Second Edition (Cold Spring Harbor Laboratories, New York, 1989). In a preferred embodiment of the invention, polymerase chain reactions (PCR) may be used to amplify fragments of DNA to be used as template DNA as described in Innis et al., ed. PCR Protocols (Academic Press, New York, 1990).

The amount of DNA template needed for accurate detection of the polymerase reaction will depend on the detection technique used. For example, for optical detection, e.g., fluorescence or chemiluminescence detection, relatively small quantities of DNA in the femtomole range are needed. For thermal detection quantities approaching one picomole may be required to detect the change in temperature resulting from a DNA polymerase mediated extension reaction.

In enzymatic sequencing reactions, the priming of DNA synthesis is achieved by the use of an oligonucleotide primer with a base sequence that is complementary to, and therefore capable of binding to, a specific region on the template DNA sequence. In instances where the template DNA is obtained as single stranded DNA from bacteriophage, or as double stranded DNA derived from plasmids, "universal" primers that are complementary to sequences in the vectors, i.e., the bacteriophage, cosmid and plasmid vectors, and that flank the template DNA, can be used.

Primer oligonucleotides are chosen to form highly stable duplexes that bind to the template DNA sequences and remain intact during any washing steps during the extension cycles. Preferably, the length of the primer oligonucleotide is from 18–30 nucleotides and contains a balanced base composition. The structure of the primer should also be analyzed to confirm that it does not contain regions of dyad symmetry which can fold and self anneal to form secondary structures thereby rendering the primers inefficient. Conditions for selecting appropriate hybridization conditions for binding of the oligonucleotide primers in the template systems will depend on the primer sequence and are well known to those of skill in the art.

In utilizing the reactive sequencing method of the invention, a variety of different DNA polymerases may be used to incorporate dNTPs onto the 3' end of the primer which is hybridized to the template DNA molecule. Such DNA polymerases include but are not limited to Taq polymerase, T7 or T4 polymerase, and Klenow polymerase. In a preferred embodiment of the invention, described in detail below, DNA polymerases lacking 5'-3'-exonuclease proofreading activity are used in the sequencing reactions. For the most rapid reaction kinetics, the amount of polymerase is sufficient to ensure that each DNA molecule carries a non-covalently attached polymerase molecule during reaction. For a typical equilibrium constant of ~50 nM for the dissociation equilibrium:

the desired condition is: $[Pol] \geqq 50$ nM+[DNA].

In addition, reverse transcriptase which catalyzes the synthesis of single stranded DNA from an RNA template may be utilized in the reactive sequencing method of the invention to sequence messenger RNA (mRNA). Such a method comprises sequentially contacting an RNA template annealed to a primer (RNA primer/template) with dNTPs in the presence of reverse transcriptase enzyme to determine the sequence of the RNA. Because mRNA is produced by RNA polymerase-catalyzed synthesis from a DNA template, and thus contains the sequence information of the DNA template strand, sequencing the mRNA yields the sequence of the DNA gene from which it was transcribed. Eukaryotic mRNAs have poly(A) tails and therefore the primer for reverse transcription can be an oligo(dT). Typically, it will be most convenient to synthesize the oligo(dT) primer with a terminal biotin or amino group through which the primer can be captured on a substrate and subsequently hybridize to and capture the template mRNA strand.

The extension reactions are carried out in buffer solutions which contain the appropriate concentrations of salts, dNTPs and DNA polymerase required for the DNA polymerase mediated extension to proceed. For guidance regarding such conditions see, for example, Sambrook et al., (1989, Molecular Cloning, A Laboratory Manual. Cold Spring Harbor Press, N.Y.); and Ausubel et al. (1989, Current Protocols in Molecular Biology, Green Publishing Associates and Wiley Interscience, N.Y.).

Typically, buffer containing one of the four dNTPs is added into a reaction cell. Depending on the identity of the nucleoside base at the next unpaired template site in the primer/template system, a reaction will occur when the reaction cell contains the appropriate dNTP. When the reaction cell contains any one of the other three incorrect dNTPs, no reaction will take place.

The reaction cell is then flushed with dNTP free buffer and the cycle is repeated until a complete DNA sequence is identified. Detection of a DNA polymerase mediated extension can be made using any of the detection methods described in detail below including optical and thermal detection of an extension reaction.

In a preferred embodiment of the invention, the primer/template system comprises the template DNA tethered to a solid phase support to permit the sequential addition of sequencing reaction reagents without complicated and time consuming purification steps following each extension reaction. Preferably, the template DNA is covalently attached to a solid phase support, such as the surface of a reaction flow cell, a polymeric microsphere, filter material, or the like, which permits the sequential application of sequencing reaction reagents, i.e., buffers, dNTPs and DNA polymerase, without complicated and time consuming purification steps following each extension reaction. Alternatively, for applications that require sequencing of many samples containing the same vector template or same gene, for example, in diagnostic applications, a universal primer may be tethered to a support, and the template DNA allowed to hybridize to the immobilized primer.

The DNA may be modified to facilitate covalent or non-covalent tethering of the DNA to a solid phase support. For example, when PCR is used to amplify DNA fragments, the 5' ends of one set of PCR primer oligonucleotides strands may be modified to carry a linker moiety for tethering one of the two complementary types of DNA strands produced to a solid phase support. Such linker moieties include, for example, biotin. When using biotin, the biotinylated DNA fragments may be bound non-covalently to streptavidin covalently attached to the solid phase support. Alternatively, an amino group ($-NH_2$) may be chemically incorporated into one of the PCR primer strands and used to covalently link the DNA template to a solid phase support using standard chemistry, such as reactions with N-hydroxysuccinimide activated agarose surfaces.

In another embodiment, the 5' ends of the sequencing oligonucleotide primer may be modified with biotin, for non-covalent capture to a streptavidin-treated support, or with an amino group for chemical linkage to a solid support; the template strands are then captured by the non-covalent binding attraction between the immobilized primer base sequence and the complementary sequence on the template strands. Methods for immobilizing DNA on a solid phase support are well known to those of skill in the art and will vary depending on the solid phase support chosen.

In the reactive sequencing method of the present invention, DNA polymerase is presented sequentially with each of the 4 dNTPs. In the majority of the reaction cycles, only incorrect dNTPs will be present, thereby increasing the likelihood of misincorporation of incorrect nucleotides into the extending DNA primer/template system.

Accordingly, the present invention further provides methods for optimizing the reactive sequencing reaction to achieve rapid and complete incorporation of the correct nucleotide into the DNA primer/template system, while limiting the misincorporation of incorrect nucleotides. For example, dNTP concentrations may be lowered to reduce misincorporation of incorrect nucleotides into the DNA primer. $K_m$ values for incorrect dNTPs can be as much as 1000-fold higher than for correct nucleotides, indicating that a reduction in dNTP concentrations can reduce the rate of misincorporation of nucleotides. Thus, in a preferred embodiment of the invention the concentration of dNTPs in the sequencing reactions are approximately 5–20 μM. At this concentration, incorporation rates are as close to the maximum rate of 400 nucleotides/s for T4 DNA polymerase as possible.

In addition, relatively short reaction times can be used to reduce the probability of misincorporation. For an incorporation rate approaching the maximum rate of ~400 nucleotides/s, a reaction time of approximately 25 milliseconds (ms) will be sufficient to ensure extension of 99.99% of primer strands.

In a specific embodiment of the invention, DNA polymerases lacking 3' to 5' exonuclease activity may be used for reactive sequencing to limit exonucleolytic degradation of primers that would occur in the absence of correct dNTPs. In the presence of all four dNTPs, misincorporation frequencies by DNA polymerases possessing exonucleolytic proofreading activity are as low as one error in $10^6$ to $10^8$ nucleotides incorporated as discussed in Echols and Goodman (1991, Annu. Rev. Biochem. 60;477–511); and Goodman et al. (1993, Crit. Rev. Biochem. Molec. Biol. 28:83–126); and Loeb and Kunkel (1982, Annu. Rev. Biochem. 52:429–457). In the absence of proofreading, DNA polymerase error rates are typically on the order of 1 in $10^4$ to 1 in $10^6$. Although exonuclease activity increases the fidelity of a DNA polymerase, the use of DNA polymerases having proofreading activity can pose technical difficulties for the reactive sequencing method of the present invention. Not only will the exonuclease remove any misincorporated nucleotides, but also, in the absence of a correct dNTP complementary to the next template base, the exonuclease will remove correctly-paired nucleotides successively until a point on the template sequence is reached where the base is complementary to the dNTP in the reaction cell. At this point, an idling reaction is established where the polymerase repeatedly incorporates the correct dNMP and then removes it. Only when a correct dNTP is present will the rate of polymerase activity exceed the exonuclease rate so that an idling reaction is established that maintains the incorporation of that correct nucleotide at the 3' end of the primer.

A number of T4 DNA polymerase mutants containing specific amino acid substitutions possess reduced exonuclease activity levels up to 10,000-fold less than the wild-type enzyme. For example, Reha-Krantz and Nonay (1993, J. Biol. Chem. 268:27100–17108) report that when Asp 112 was replaced with Ala and Glu 114 was replaced with Ala (D112A/E114A) in T4 polymerase, these two amino acid substitutions reduced the exonuclease activity on double stranded DNA by a factor of about 300 relative to the wild type enzyme. Such mutants may be advantageously used in the practice of the invention for incorporation of nucleotides into the DNA primer/template system.

In yet another embodiment of the invention, DNA polymerases which are more accurate than wild type polymerases at incorporating the correct nucleotide into a DNA primer/template may be used. For example, in a (D112A/E114A) mutant T4 polymerase with a third mutation where Ile 417 is replaced by Val (I417V/D112A/E114A), the I417V mutation results in an antimutator phenotype for the polymerase (Reha-Krantz and Nonay, 1994, J. Biol. Chem. 269:5635–5643; Stocki et al., 1995, Mol. Biol. 254:15–28). This antimutator phenotype arises because the polymerase tends to move the primer ends from the polymerase site to the exonuclease site more frequently and thus proof read more frequently than the wild type polymerase, and thus increases the accuracy of synthesis.

In yet another embodiment of the invention, polymerase mutants that are capable of more efficiently incorporating fluorescent-labeled nucleotides into the template DNA system molecule may be used in the practice of the invention. The efficiency of incorporation of fluorescent-labeled nucleotides may be reduced due to the presence of bulky fluorophore labels that may inhibit dNTP interaction at the active site of the polymerase. Polymerase mutants that may be advantageously used for incorporation of fluorescent-labeled dNTPs into DNA include but are not limited to those described in U.S. application Ser. No. 08/632,742 filed Apr. 16, 1996 which is incorporated by reference herein.

In a preferred embodiment of the invention, the reactive sequencing method utilizes a two cycle system. An exonuclease-deficient polymerase is used in the first cycle and a mixture of exonuclease-deficient and exonuclease-proficient enzymes are used in the second cycle. In the first cycle, the primer/template system together with an exonuclease-deficient polymerase will be presented sequentially with each of the four possible nucleotides. Reaction time and conditions will be such that a sufficient fraction of primers are extended to allow for detection and quantification of nucleotide incorporation, ~98%, for accurate quantification of multiple single-base repeats. In the second cycle, after identification of the correct nucleotide, a mixture of exonuclease proficient and deficient polymerases, or a polymerase containing both types of activity will be added in a second cycle together with the correct dNTP identified in the first cycle to complete and proofread the primer extension. In this way, an exonuclease-proficient polymerase is only present in the reaction cell when the correct dNTP is present, so that exonucleolytic degradation of correctly extended strands does not occur, while degradation and correct re-extension of previously incorrectly extended strands does occur, thus achieving extremely accurate strand extension.

The detection of a DNA polymerase mediated extension reaction can be accomplished in a number of ways. For example, the heat generated by the extension reaction can be measured using a variety of different techniques such as those employing thermopile, thermistor and refractive index measurements.

In an embodiment of the invention, the heat generated by a DNA polymerase mediated extension reaction can be measured. For example, in a reaction cell volume of 100 micrometers$^3$ containing 1 µg of water as the sole thermal mass and $2 \times 10^{11}$ DNA template molecules (300 fmol) tethered within the cell, the temperature of the water increases by $1 \times 10^{3 \circ}$ C. for a polymerase reaction which extends the primer by a single nucleoside monophosphate. This calculation is based on the experimental determination that a one base pair extension in a DNA chain is an exothermic reaction and the enthalpy change associated with this reaction is 3.5 kcal/mole of base. Thus extension of 300 fmol of primer strands by a single base produces 300 fmol×3.5 kcal/mol or $1 \times 10^{-9}$ cal of heat. This is sufficient to raise the temperature of 1 µg of water by $1 \times 10^{-3 \circ}$ C. Such a temperature change can be readily detectable using thermistors (sensitivity $\leq 10^{-4 \circ}$ C.); thermopiles (sensitivity $\leq 10^{-5 \circ}$ C.); and refractive index measurements (sensitivity $\leq 10^{-6 \circ}$ C.).

In a specific embodiment of the invention, thermopiles may used to detect temperature changes. Such thermopiles are known to have a high sensitivity to temperature and can make measurements in the tens of micro-degree range in several second time constants. Thermopiles may be fabricated by constructing serial sets of junctions of two dissimilar metals and physically arranging the junctions so that alternating junctions are separated in space. One set of junctions is maintained at a constant reference temperature, while the alternate set of junctions is located in the region whose temperature is to be sensed. A temperature difference between the two sets of junctions produces a potential difference across the junction set which is proportional to the temperature difference, to the thermoelectric coefficient of the junction and to the number of junctions. For optimum response, bimetallic pairs with a large thermoelectric coefficient are desirable, such as bismuth and antimony. Thermopiles may be fabricated using thin film deposition techniques in which evaporated metal vapor is deposited onto insulating substrates through specially fabricated masks. Thermopiles that may be used in the practice of the invention include thermopiles such as those described in U.S. Pat. No. 4,935,345, which is incorporated by reference herein.

In a specific embodiment of the invention, miniature thin film thermopiles produced by metal evaporation techniques, such as those described in U.S. Pat. No. 4,935,345 incorporated herein by reference, may be used to detect the enthalpy changes. Such devices have been made by vacuum evaporation through masks of about 10 mm square. Using methods of photolithography, sputter etching and reverse lift-off techniques, devices as small as 2 mm square may be constructed without the aid of modem microlithographic techniques. These devices contain 150 thermoelectric junctions and employ 12 micron line widths and can measure the exothermic heat of reaction of enzyme-catalyzed reactions in flow streams where the enzyme is preferably immobilized on the surface of the thermopile.

To incorporate thermopile detection technology into a reactive sequencing device, thin-film bismuth-antimony thermopiles 2, as shown in FIG. 1, may be fabricated by successive electron-beam evaporation of bismuth and antimony metals through two different photolithographically-generated masks in order to produce a zigzag array of alternating thin bismuth and antimony wires which are connected to form two sets of bismuth-antimony thermocouple junctions. Modern microlithographic techniques will allow fabrication of devices at least one order of magnitude smaller than those previously made, i.e., with line widths as small as 1 µm and overall dimensions on the order of 100 µm$^2$. One set of junctions 4 (the sensor junctions) is located within the reaction cell 6, i.e., deposited on a wall of the reaction cell, while the second reference set of junctions 8 is located outside the cell at a reference point whose temperature is kept constant. Any difference in temperature between the sensor junctions and the reference junctions results in an electric potential being generated across the device, which can be measured by a high-resolution digital voltmeter 10 connected to measurement points 12 at either end of the device. It is not necessary that the temperature of the reaction cell and the reference junctions be the same in the absence of a polymerase reaction event, only that a change in the temperature of the sensor junctions due to a polymerase reaction event be detectable as a change in the voltage generated across the thermopile.

Figure 2:
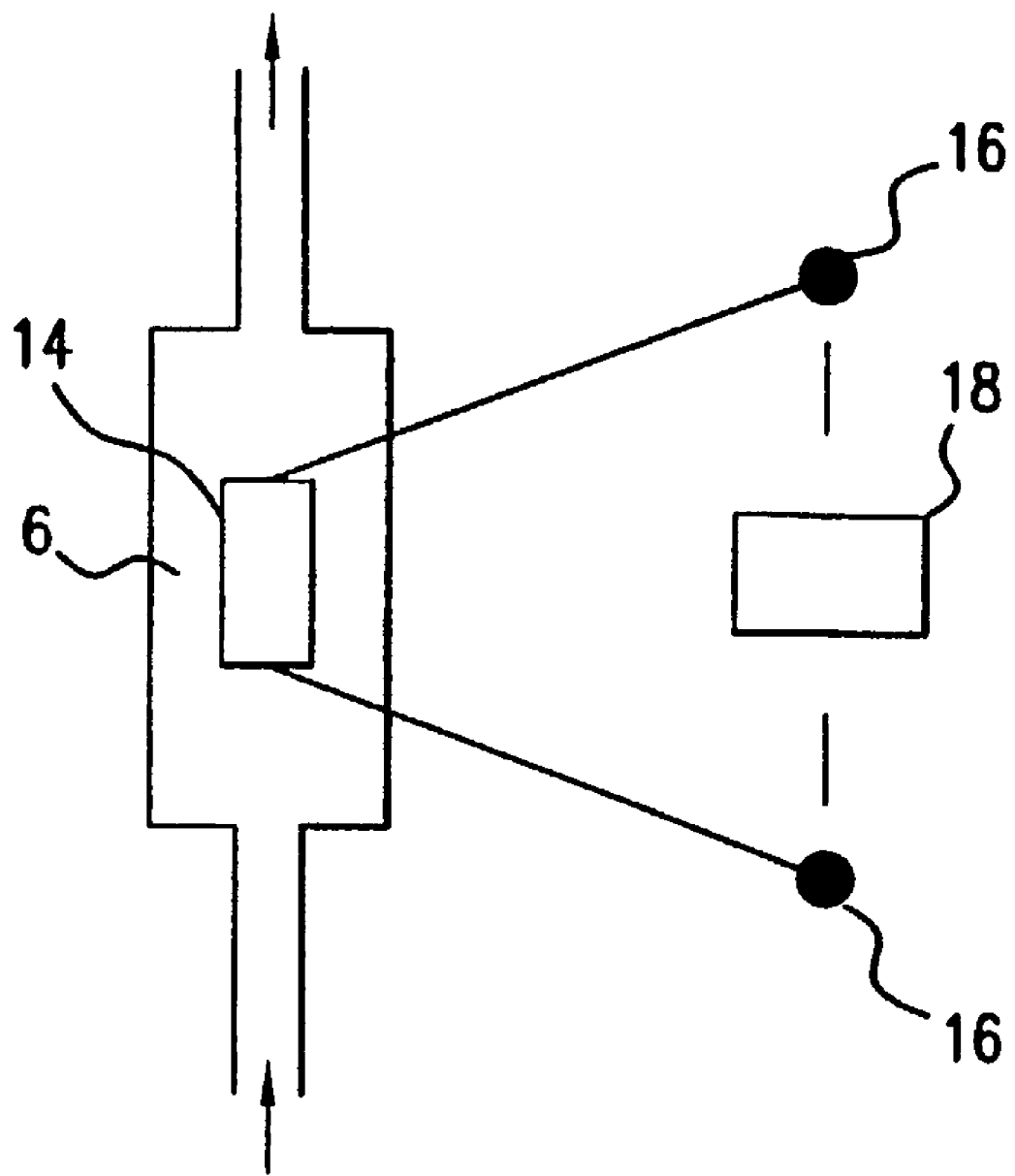
FIG. 2 is a schematic diagram of a reactive sequencing device containing a thermistor in accordance with the invention.

In addition to thermopiles, as shown in FIG. 2, a thermistor 14 may also be used to detect temperature changes in the reaction cell 6 resulting from DNA polymerase mediated incorporation of dNMPs into the DNA primer strand. Thermistors are semiconductors composed of a sintered mixture of metallic oxides such as manganese, nickel, and cobalt oxides. This material has a large temperature coefficient of resistance, typically ~4% per ° C., and so can sense extremely small temperature changes when the resistance is monitored with a stable, high-resolution resistance-measuring device such as a digital voltmeter, e.g., Keithley Instruments Model 2002. A thermistor 14, such as that depicted in FIG. 2, may be fabricated in the reactive sequencing reaction cell by sputter depositing a thin film of the active thermistor material onto the surface of the reaction cell from a single target consisting of hot pressed nickel, cobalt and manganese oxides. Metal interconnections 16 which extend out beyond the wall of the reaction cell may also be fabricated in a separate step so that the resistance of the thermistor may be measured using an external measuring device 18.

Temperature changes may also be sensed using a refractive index measurement technique. For example, techniques such as those described in Bornhop (1995, Applied Optics 34:3234–323) and U.S. Pat. No. 5,325,170, may be used to detect refractive index changes for liquids in capillaries. In such a technique, a low-power He—Ne laser is aimed off-center at a right angle to a capillary and undergoes multiple internal reflection. Part of the beam travels through the liquid while the remainder reflects only off the external capillary wall. The two beams undergo different phase shifts depending on the refractive index difference between the liquid and capillary. The result is an interference pattern, with the fringe position extremely sensitive to temperature-induced refractive index changes.

In a further embodiment of the invention, the thermal response of the system may be increased by the presence of inorganic pyrophosphatase enzyme which is contacted with the template system along with the dNTP solution. Additionally, heat is released as the pyrophosphate released from the dNTPs upon incorporation into the template system is hydrolyzed by inorganic pyrophosphatase enzyme.

In another embodiment, the pyrophosphate released upon incorporation of dNTP's may be removed from the template system and hydrolyzed, and the resultant heat detected, using thermopile, thermistor or refractive index methods, in a separate reaction cell downstream. In this reaction cell, inorganic pyrophosphatase enzyme may be mixed in solution with the dNTP removed from the DNA template system, or alternatively the inorganic pyrophosphatase enzyme may be covalently tethered to the wall of the reaction cell.

Alternatively, the polymerase-catalyzed incorporation of a nucleotide base can be detected using fluorescence and chemiluminescence detection schemes. The DNA polymerase mediated extension is detected when a fluorescent or chemiluminescent signal is generated upon incorporation of a fluorescently or chemiluminescently labeled dNMP into the extending DNA primer strand. Such tags are attached to the nucleotide in such a way as to not interfere with the action of the polymerase. For example, the tag may be attached to the nucleotide base by a linker arm sufficiently long to move the bulky fluorophore away from the active site of the enzyme.

For use of such detection schemes, nucleotide bases are labeled by covalently attaching a compound such that a fluorescent or chemiluminescent signal is generated following incorporation of a dNTP into the extending DNA primer/template. Examples of fluorescent compounds for labeling dNTPs include but are not limited to fluorescein, rhodamine, and BODIPY (4,4-difluoro-4-bora-3a,4a-diaza-s-indacene). See Handbook of Molecular Probes and Fluorescent Chemicals available from Molecular Probes, Inc. (Eugene, Oreg.). Examples of chemiluminescence based compounds that may be used in the sequencing methods of the invention include but are not limited to luminol and dioxetanones (See, Gunderman and McCapra, "Chemiluminescence in Organic Chemistry", Springer-Verlag, Berlin Heidelberg, 1987)

Fluorescently or chemiluminescently labeled dNTPs are added individually to a DNA template system containing template DNA annealed to the primer, DNA polymerase and the appropriate buffer conditions. After the reaction interval, the excess dNTP is removed and the system is probed to detect whether a fluorescent or chemiluminescent tagged nucleotide has been incorporated into the DNA template. Detection of the incorporated nucleotide can be accomplished using different methods that will depend on the type of tag utilized.

For fluorescently-tagged dNTPs the DNA template system may be illuminated with optical radiation at a wavelength which is strongly absorbed by the tag entity. Fluorescence from the tag is detected using for example a photodetector together with an optical filter which excludes any scattered light at the excitation wavelength.

Since labels on previously incorporated nucleotides would interfere with the signal generated by the most recently incorporated nucleotide, it is essential that the fluorescent tag be removed at the completion of each extension reaction. To facilitate removal of a fluorescent tag, the tag may be attached to the nucleotide via a chemically or photochemically cleavable linker using methods such as those described by Metzger, M. L. et al. (1994, Nucleic Acids Research 22:4259–4267) and Burgess, K. et al., (1997, J. Org. Chem. 62:5165–5168) so that the fluorescent tag may be removed from the DNA template system before a new extension reaction is carried out.

In a further embodiment utilizing fluorescent detection, the fluorescent tag is attached to the dNTP by a photocleavable or chemically cleavable linker, and the tag is detached following the extension reaction and removed from the template system into a detection cell where the presence, and the amount, of the tag is determined by optical excitation at a suitable wavelength and detection of fluorescence. In this embodiment, the possibility of fluorescence quenching, due to the presence of multiple fluorescent tags immediately adjacent to one another on a primer strand which has been extended complementary to a single base repeat region in the template, is minimized, and the accuracy with which the repeat number can be determined is optimized. In addition, excitation of fluorescence in a separate chamber minimizes the possibility of photolytic damage to the DNA primer/template system.

In a further embodiment of the technique, the response generated by a DNA polymerase-mediated extension reaction can be amplified. In this embodiment, the dNTP is chemically modified by the covalent attachment of a signaling tag through a linker that can be cleaved either chemically or photolytically. Following exposure of the dNTP to the primer/template system and flushing away any unincorporated chemically modified dNTP, any signaling tag that has been incorporated is detached by a chemical or photolytic reaction and flushed out of the reaction chamber to an amplification chamber in which an amplified signal may be produced and detected.

A variety of methods may be used to produce an amplified signal. In one such method the signaling tag has a catalytic function. When the catalytic tag is cleaved and allowed to react with its substrate, many cycles of chemical reaction ensue producing many moles of product per mole of catalytic tag, with a corresponding multiplication of reaction enthalpy. Either the reaction product is detected, through some property such as color or absorbency, or the amplified heat product is detected by a thermal sensor. For example, if an enzyme is covalently attached to the dNTP via a cleavable linker arm of sufficient length that the enzyme does not interfere with the active site of the polymerase enzyme. Following incorporation onto the DNA primer strand, that enzyme is detached and transported to a second reactor volume in which it is allowed to interact with its specific substrate, thus an amplified response is obtained as each enzyme molecule carries out many cycles of reaction. For example, the enzyme catalase (CAT) catalyzes the reaction:

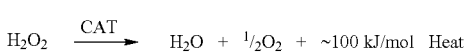

$$H_2O_2 \xrightarrow{CAT} H_2O + \tfrac{1}{2}O_2 + \sim100 \text{ kJ/mol Heat}$$

if each dNTP is tagged with a catalase molecule which is detached after dNMP incorporation and allowed to react downstream with hydrogen peroxide, each nucleotide incorporation would generate ~25 kcal/mol×N of heat where N is the number of hydrogen peroxide molecules decomposed by the catalase. The heat of decomposition of hydrogen peroxide is already ~6–8 times greater than for nucleotide incorporation, (i.e. 3.5–4 kcal/mol). For decomposition of ~100–150 hydrogen peroxide molecules the amount of heat generated per base incorporation approaches 1000 times that of the unamplified reaction. Similarly, enzymes which produce colored products, such as those commonly used in enzyme-linked immunosorbent assays (ELISA) could be incorporated as detachable tags. For example the enzyme alkaline phosphatase converts colorless p-nitrophenyl phosphate to a colored product (p-nitrophenol); the enzyme horseradish peroxidase converts colorless o-phenylenediamine hydrochloride to an orange product. Chemistries for linking these enzymes to proteins such as antibodies are well-known to those versed in the art, and could be adapted to link the enzymes to nucleotide bases via linker arms that maintain the enzymes at a distance from the active site of the polymerase enzymes.

In a further embodiment, an amplified thermal signal may be produced when the signaling tag is an entity which can stimulate an active response in cells which are attached to, or held in the vicinity of, a thermal sensor such as a thermopile or thermistor. Pizziconi and Page (1997, Biosensors and Bioelectronics 12:457–466) reported that harvested and cultured mast cell populations could be activated by calcium ionophore to undergo exocytosis to release histamine, up to 10–30 μg (100–300 fmol) per cell. The multiple cell reactions leading to exocytosis are themselves exothermic. This process is further amplified using the enzymes diamine oxidase to oxidize the histamine to hydrogen peroxide and imidazoleacetaldehyde, and catalase to disproportionate the hydrogen peroxide. Two reactions together liberate over 100 kJ of heat per mole of histamine. For example, a calcium ionophore is covalently attached to the dNTP base via a linker arm which distances the linked calcium ionophore from the active site of the polymerase enzyme and is chemically or photochemically cleavable. Following the DNA polymerase catalyzed incorporation step, and flushing away unincorporated nucleotides any calcium ionophore remaining bound to an incorporated nucleotide may be cleaved and flushed downstream to a detection chamber containing a mast cell-based sensor such as described by Pizziconi and Page (1997, Biosensors and Bioelectronics 12:457–466). The calcium ionophore would bind to receptors on the mast cells stimulating histamine release with the accompanying generation of heat. The heat production could be further amplified by introducing the enzymes diamine oxidase to oxidize the histamine to hydrogen peroxide and imidazoleacetaldehyde, and catalase to disproportionate the hydrogen peroxide. Thus a significantly amplified heat signal would be produced which could readily be detected by a thermopile or thermistor sensor within, or in contact with, the reaction chamber.

In a further embodiment utilizing chemiluminescent detection, the chemiluminescent tag is attached to the dNTP by a photocleavable or chemically cleavable linker. The tag is detached following the extension reaction and removed from the template system into a detection cell where the presence, and the amount, of the tag is determined by an appropriate chemical reaction and sensitive optical detection of the light produced. In this embodiment, the possibility of a non-linear optical response due to the presence of multiple chemiluminescent tags immediately adjacent to one another on a primer strand which has been extended complementary to a single base repeat region in the template, is minimized, and the accuracy with which the repeat number can be determined is optimized. In addition, generation of chemiluminescence in a separate chamber minimizes chemical damage to the DNA primer/template system, and allows detection under harsh chemical conditions which otherwise would chemically damage the DNA primer/template. In this way, chemiluminescent tags can be chosen to optimize chemiluminescence reaction speed, or compatibility of the tagged dNTP with the polymerase enzyme, without regard to the compatibility of the chemiluminescence reaction conditions with the DNA primer/template.

In a further embodiment of the invention, the concentration of the dNTP solution removed from the template system following each extension reaction can be measured by detecting a change in UV absorption due to a change in the concentration of dNTPs, or a change in fluorescence response of fluorescently-tagged dNTPs. The incorporation of nucleotides into the extended template would result in a decreased concentration of nucleotides removed from the template system. Such a change could be detected by measuring the UV absorption of the buffer removed from the template system following each extension cycle.

In a further embodiment of the invention, extension of the primer strand may be sensed by a device capable of sensing fluorescence from, or resolving an image of, a single DNA molecule. Devices capable of sensing fluorescence from a single molecule include the confocal microscope and the near-field optical microscope. Devices capable of resolving an image of a single molecule include the scanning tunneling microscope (STM) and the atomic force microscope (AFM).

In this embodiment of the invention, a single DNA template molecule with attached primer is immobilized on a surface and viewed with an optical microscope or an STM or AFM before and after exposure to buffer solution containing a single type of dNTP, together with polymerase enzyme and other necessary electrolytes. When an optical microscope is used, the single molecule is exposed serially to fluorescently-tagged dNTP solutions and as before incorporation is sensed by detecting the fluorescent tag after excess unreacted dNTP is removed. Again as before, the incorporated fluorescent tag must be cleaved and discarded before a subsequent tag can be detected. Using the STM or AFM, the change in length of the primer strand is imaged to detect incorporation of the dNTP. Alternatively the dNTP may be tagged with a physically bulky molecule, more readily visible in the STM or AFM., and this bulky tag is removed and discarded before each fresh incorporation reaction.

When sequencing a single molecular template in this way, the possibility of incomplete reaction producing erroneous signal and out-of-phase strand extension, does not exist and the consequent limitations on read length do not apply. For a single molecular template, reaction either occurs or it does not, and if it does not, then extension either ceases and is known to cease, or correct extension occurs in a subsequent cycle with the correct dNTP. In the event that an incorrect nucleotide is incorporated, which has the same probability as more the multiple strand processes discussed earlier, for example 1 in 1,000, an error is recorded in the sequence, but this error does not propagate or affect subsequent readout and so the read length is not limited by incorrect incorporation.

Preparation of specific embodiments in accordance with the present invention will now be described in further detail. These examples are intended to be illustrative and the invention is not limited to the specific materials and methods set forth in these embodiments.

EXAMPLE 1

Figure 3:
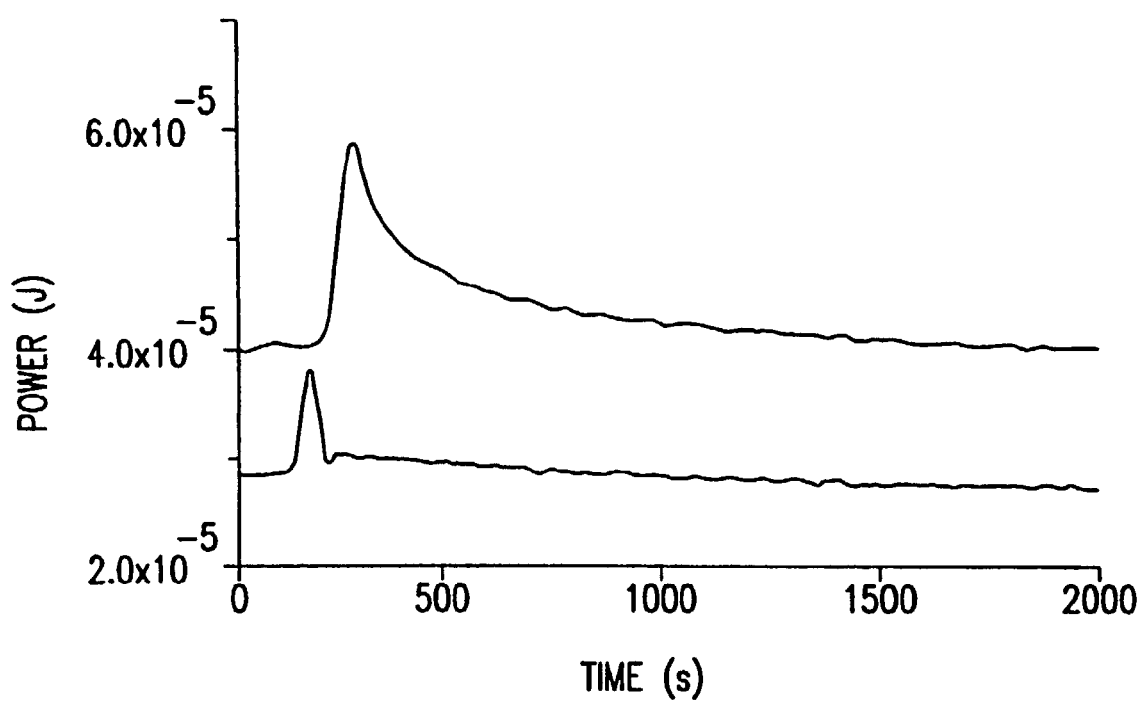
FIG. 3 is a schematic diagram illustrating a representative embodiment of microcalorimetry detection of a DNA polymerase reaction in accordance with the invention.

A microcalorimetic experiment was performed which demonstrates for the first time the successful thermal detection of a DNA polymerase reaction. The results are shown in FIG. 3. Approximately 20 units of T7 Sequenase was injected into a 3 mL reaction volume containing approximately 20 nmol of DNA template and complementary primer, and an excess of dNTPs. The primer was extended by 52-base pairs, the expected length given the size of the template. Using a commercial microcalorimeter (TAM Model 2273; Thermometrics, Sweden) a reaction enthalpy of 3.5–4 kcal per mole of base was measured (FIG. 3). This measurement is well within the value required for thermal detection of DNA polymerase activity. This measurement also demonstrates the sensitivity of thermopile detection as the maximum temperature rise in the reaction cell was $1 \times 10^{-3}$° C. The lower trace seen in FIG. 3 is from a reference cell showing the injection artifact for an enzyme-free injection into buffer containing no template system.

EXAMPLE 2

To illustrate the utility of mutant T4 polymerases, two primer extension assays were performed with two different mutant T4 polymerases, both of which are exonuclease deficient. In one mutant, Asp112 is replaced with Ala and Glu114 is replaced with Ala (D112A/E114A). The exonuclease activity of this mutant on double-stranded DNA is reduced by a factor of about 300 relative to the wild type enzyme as described by Reha-Krantz and Nonay (1993, J. Biol. Chem. 268:27100–27108). In a second polymerase mutant, in addition to the D112A/E114A amino acid substitutions, a third substitution replaces Ile417 with Val (I417V/D112A/E114A). The I417V mutation increases the accuracy of synthesis by this polymerase (Stocki, S. A. and Reha-Krantz, L. J, 1995, J. Mol. Biol. 245:15–28;Reha-Krantz, L. J. and Nonay, R. L., 1994, J. Biol. Chem. 269:5635–5643)

Two separate primer extension reactions were carried out using each of the polymerase mutants. In the first, only a single correct nucleotide, dGTP, corresponding to a template C was added. The next unpaired template site is a G so that misincorporation would result in formation of a G•G mispair. A G•G mispair tends to be among the most difficult mispairs for polymerases to make. In the second primer extension reaction, two nucleotides, dGTP and dCTP, complementary to the first three unpaired template sites were added. Following correct incorporation of dGMP and dCMP, the next available template site is a T. Formation of C•T mispairs tend to be very difficult while G•T mispairs tend to be the most frequent mispairs made by polymerases.

Figure 4:
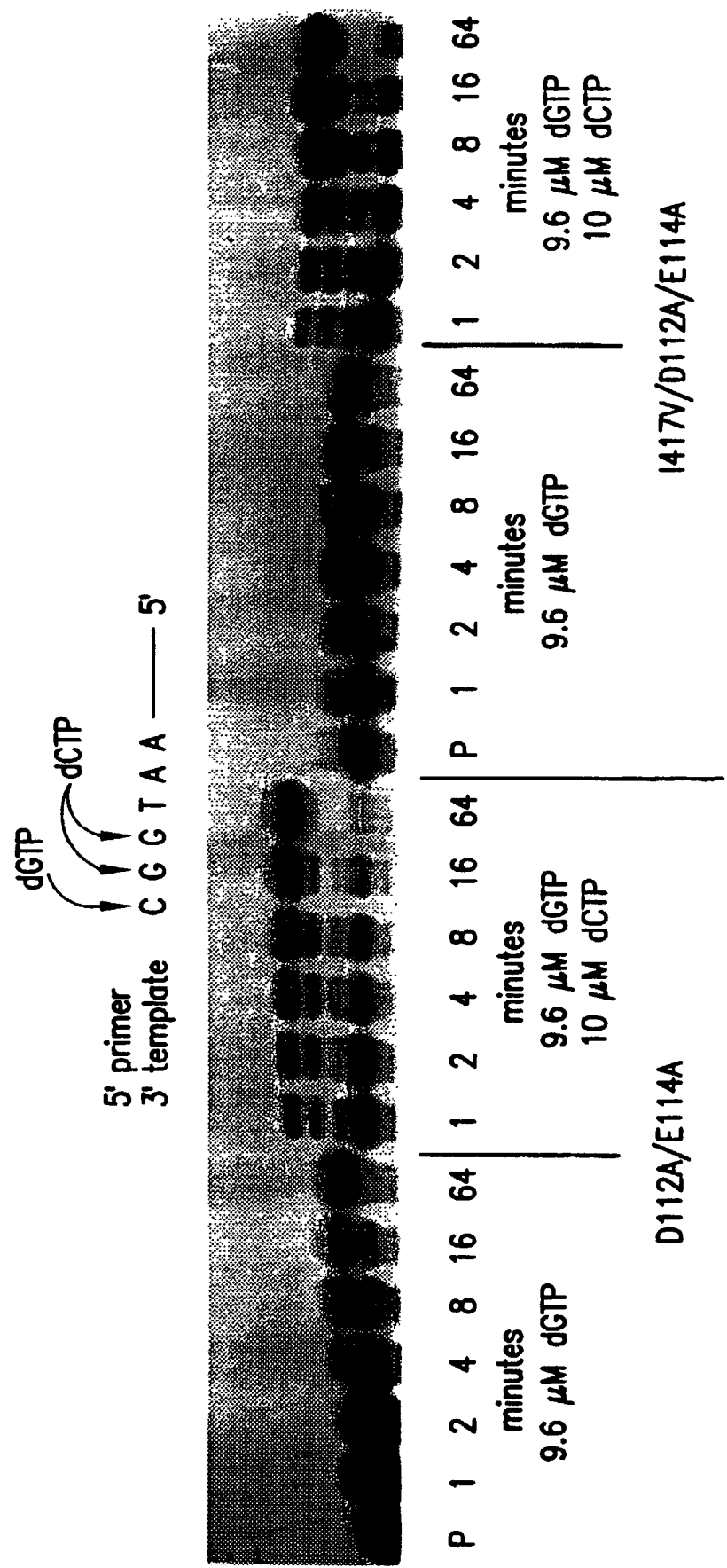
FIG. 4 is an electrophoretic gel showing a time course for primer extension assays catalyzed by T4 DNA polymerase mutants.

Time courses for primer extension reactions by both mutant T4 polymerases are shown in FIG. 4. Low concentrations of T4 polymerase relative to primer/template (p/t) were used so that incorporation reactions could be measured on convenient time scales (60 min). By 64 minutes 98% of the primers were extended. In reactions containing only dGTP, both polymerases nearly completely extended primer ends by dGMP without any detectable incorporation of dGMP opposite G. In reactions containing both dGMP and dCMP, both polymerases nearly completely extended primer ends by addition of one dGMP and two dCMP's. A small percentage (≈1%) of misincorporation was detectable in the reaction catalyzed by the D112A/E114A mutant. Significantly, no detectable misincorporation was seen in the reaction catalyzed by the I417V/D112A/E114A mutant.

EXAMPLE 3

In accordance with the invention a fluorescent tag may be attached to the nucleotide base at a site other than the 3' position of the sugar moiety. Chemistries for such tags which do not interfere with the activity of the DNA polymerase have been developed as described by Goodwin et al. (1995, Experimental Technique of Physics 41:279–294). Generally the tag is attached to the base by a linker arm of sufficient length to move the bulky tag out of the active site of the enzyme during incorporation.

Figure 5:
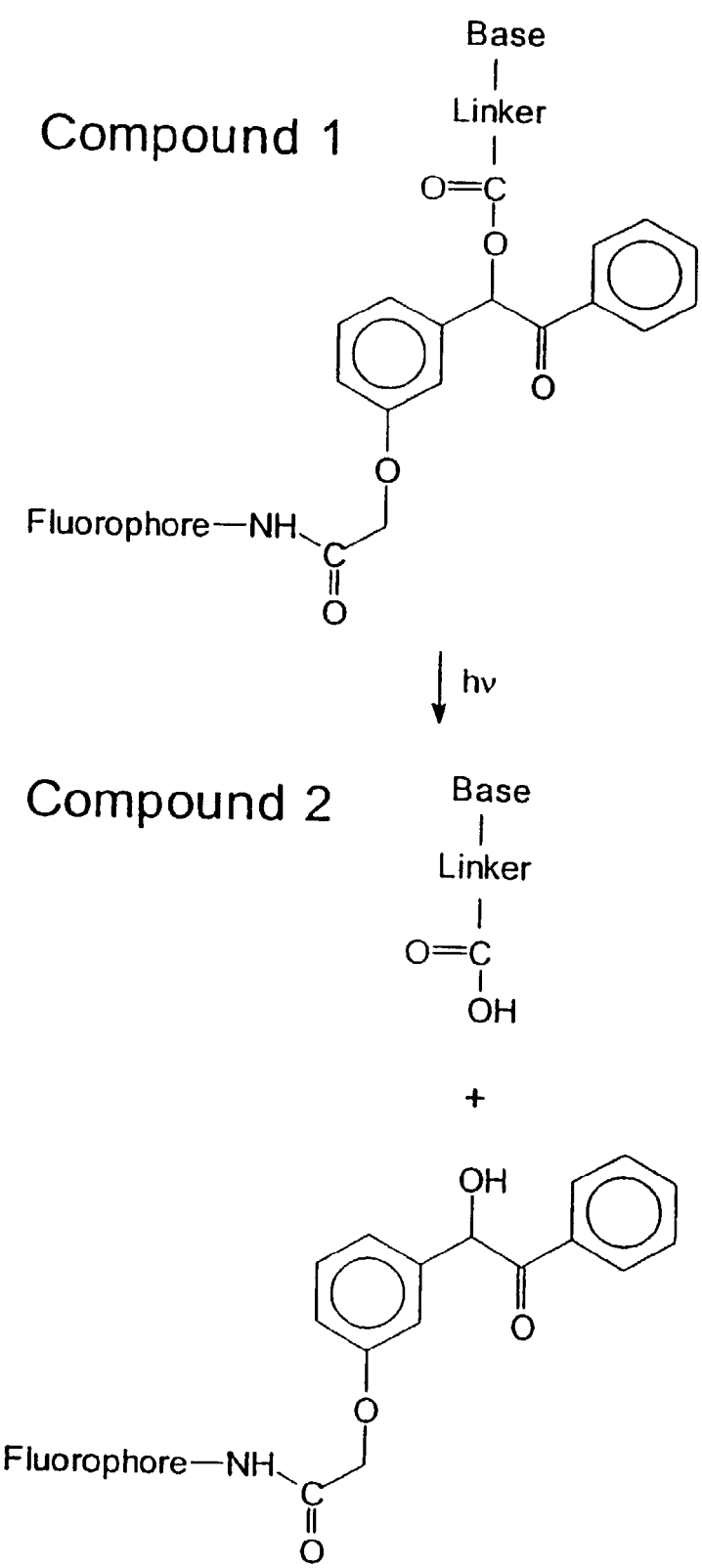
FIG. 5 is a schematic diagram illustrating a nucleotide attached to a fluorophore by a benzoin ester which is a photocleavable linker for use in the invention.

As illustrated in FIG. 5, a nucleotide can be connected to a fluorophore by a photocleavable linker, e.g., a benzoin ester. After the tagged dNMP is incorporated onto the 3' end of the DNA primer strand, the DNA template system is illuminated by light at a wave length corresponding to the absorption maximum of the fluorophore and the presence of the fluorophore is signaled by detection of fluorescence at the emission maximum of the fluorophore. Following detection of the fluorophore, the linker may be photocleaved to produce compound 2; the result is an elongated DNA molecule with a modified but non-fluorescent nucleotide attached. Many fluorophores, including for example, a dansyl group or acridine, etc., will be employed in the methodology illustrated by FIG. 5.

Alternatively, the DNA template system is not illuminated to stimulate fluorescence. Instead, the photocleavage reaction is carried out to produce compound 2 releasing the fluorophore, which is removed from the template system into a separate detection chamber. There the presence of the fluorophore is detected as before, by illumination at the absorption maximum of the fluorophore and detection of emission near the emission maximum of the fluorophore.

EXAMPLE 4

Figure 6:
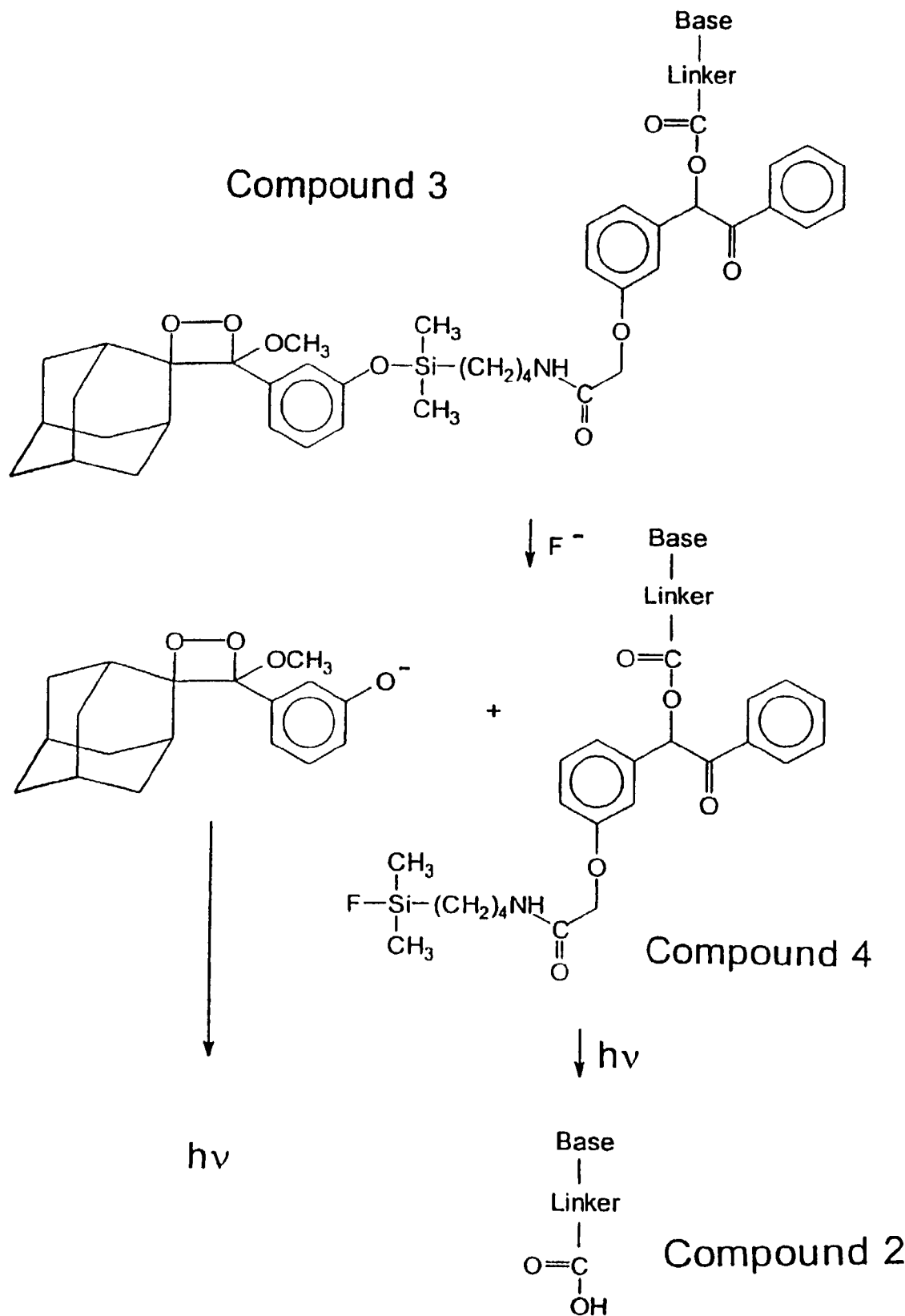
FIG. 6 is a schematic illustration of a nucleotide attached to a chemiluminescent tag for use in the invention.

In a specific embodiment of the invention, a linked system consisting of a chemiluminescently tagged dNTP can consist of a chemiluminescent group (the dioxetane portion of compound 4), a chemically cleavable linker (the silyl ether), and an optional photocleavable group (the benzoin ester) as depicted in FIG. 6. The cleavage of the silyl ether by a fluoride ion produces detectable chemiluminescence as described in Schaap et al. (1991, "Chemical and Enzymatic Triggering of 1,2-dioxetanes: Structural Effects on Chemiluminescence Efficiency" in Bioluminescence & Chemiluminescence, Stanley, P. E. and Knicha, L. J. (Eds), Wiley, N.Y. 1991, pp. 103–106). In addition, the benzoin ester that links the nucleoside triphosphate to the silyl linker is photocleavable as set forth in Rock and Chan (1996, J. Org. Chem. 61: 1526–1529); and Felder, et al. (1997, First International Electronic Conference on Synthetic Organic Chemistry, September 1–30). Having both a chemiluminescent tag and a photocleavable linker is not always necessary; the silyl ether can be attached directly to the nucleotide base and the chemiluminescent tag is destroyed as it is read.

As illustrated in FIG. 6 with respect to compound 3, treatment with fluoride ion liberates the phenolate ion of the adamantyl dioxetane, which is known to chemiluminesce with high efficiency (Bronstein et al., 1991, "Novel Chemiluminescent Adamantyl 1,2-dioxetane Enzyme Substrates," in Bioluminescence & Chemiluminescence, Stanley, P. E. and Kricka, R. J. (eds), Wiley, N.Y. 1991 pp. 73–82). The other product of the reaction is compound 4, which is no longer chemiluminescent. Compound 4 upon photolysis at 308–366 nm liberates compound 2.

The synthesis of compound 1 is achieved by attachment of the fluorophore to the carboxyl group of the benzoin, whose α-keto hydroxyl group is protected by 9-fluorenyl-methoxycarbonyl (FMOC), followed by removal of the FMOC protecting group and coupling to the nucleotide bearing an activated carbonic acid derivative at its 3' end. Compound 4 is prepared via coupling of the vinyl ether form of the adamantyl phenol, to chloro(3-cyanopropyl)dimethylsilane, reduction of the cyano group to the amine, generation of the oxetane, and coupling of this chemiluminescence precursor to the nucleotide bearing an activated carbonic acid derivative at its 3' end.

Figure 7:
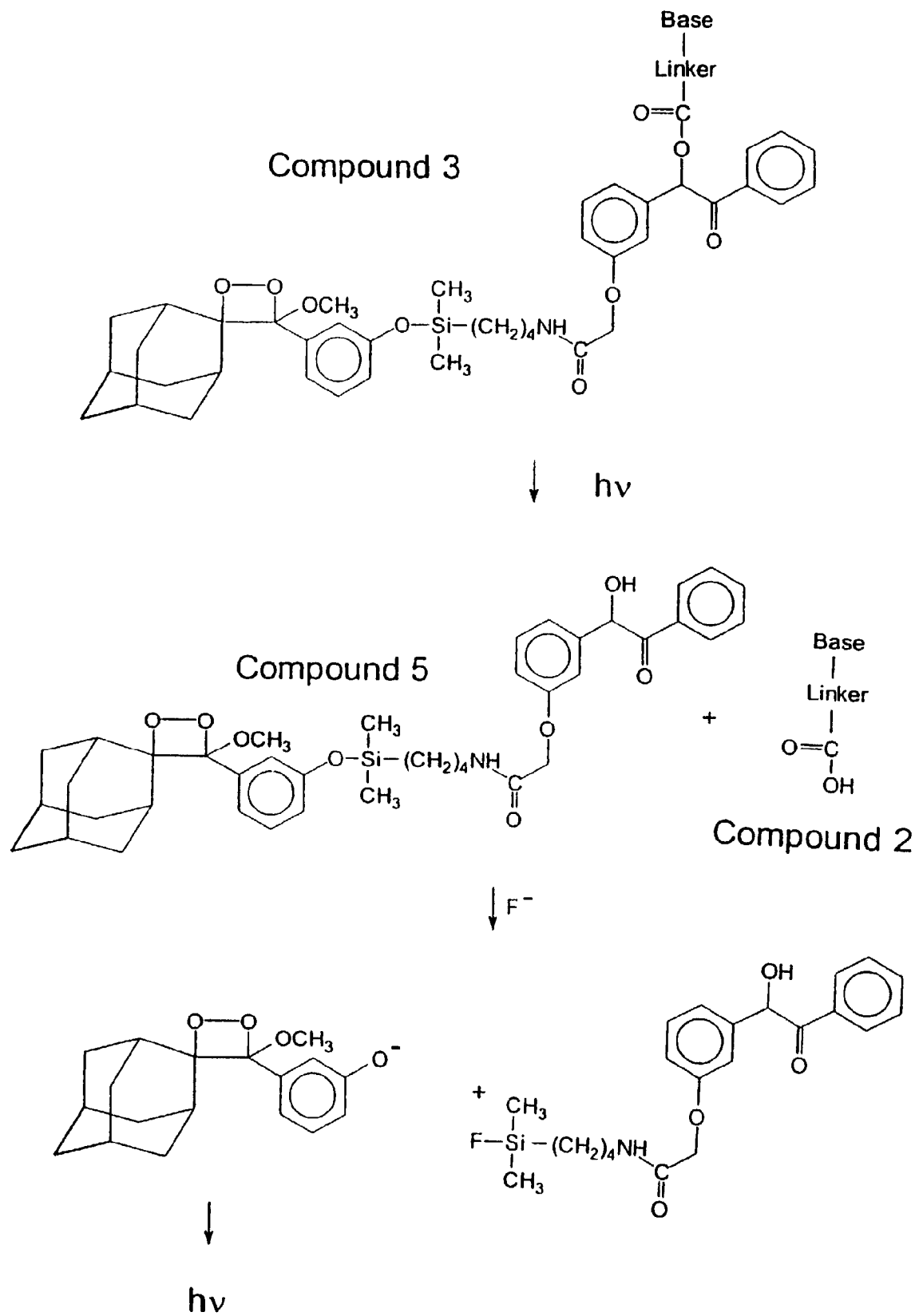
FIG. 7 is a schematic diagram of a nucleotide attached to a chemiluminescent tag by a cleavable linkage.

The chemiluminescent tag can also be attached to the dNTP by a cleavable linkage and cleaved prior to detection of chemiluminescence. As shown in FIG. 7, the benzoin ester linkage in compound 3 may be cleaved photolytically to produce the free chemiluminescent compound 5. Reaction of compound 5 with fluoride ion to generate chemiluminescence may then be carried out after compound 5 has been flushed away from the DNA template primer in the reaction chamber. As an alternative to photolytic cleavage, the tag may be attached by a chemically cleavable linker which is cleaved by chemical processing which does not trigger the chemiluminescent reaction.

EXAMPLE 5

In this example, the nucleotide sequence of a template molecule comprising a portion of DNA of unknown sequence is determined. The DNA of unknown sequence is cloned into a single stranded vector such as M13. A primer that is complementary to a single stranded region of the vector immediately upstream of the foreign DNA is annealed to the vector and used to prime synthesis in reactive sequencing. For the annealing reaction, equal molar ratios of primer and template (calculated based on the approximation that one base contributes 330 g/mol to the molecular weight of a DNA polymer) is mixed in a buffer consisting of 67 mM TrisHCl pH 8.8, 16.7 mM $(NH_4)_2SO_4$, and 0.5 mM EDTA. This buffer is suitable both for annealing DNA and subsequent polymerase extension reactions. Annealing is accomplished by heating the DNA sample in buffer to 80° C., and allowing it to slowly cool to room temperature. Samples are briefly spun in a microcentrifuge to remove condensation from the lid and walls of the tube. To the DNA is added 0.2 mol equivalents of T4 polymerase mutant I417V/D112A/E114A and buffer components so that the final reaction cell contains 67 mM TrisHCl pH 8.8, 16.7 mM $(NH_4)_2SO_4$, 6.7 mM $MgCl_2$ and 0.5 mM dithiothreitol. The polymerase is then queried with one dNTP at a time at a final concentration of 10 μM. The nucleotide is incubated with polymerase at 37° C. for 10 s. Incorporation of dNTPs may be detected by one of the methods described above including measuring fluorescence, chemiluminescence or temperature change. The reaction cycle will be repeated with each of the four dNTPs until the complete sequence of the DNA molecule has been determined.

EXAMPLE 6

FIG. 7 illustrates a mechanical fluorescent sequencing method in accordance with the invention. A DNA template and primer are captured onto beads 18 using, for example, avidin-biotin or —NH$_2$/n-hydroxysuccinimide chemistry and loaded behind a porous frit or filter 20 at the tip of a micropipette 22 or other aspiration device as shown in FIG. 7(a), step 1. Exonuclease deficient polymerase enzyme is added and the pipette tip is lowered into a small reservoir 24 containing a solution of fluorescently-labelled dNTP. As illustrated in step 2 of FIG. 7(a), a small quantity of dNTP solution is aspirated through the filter and allowed to react with the immobilized DNA. The dNTP solution also contains approximately 100 nM polymerase enzyme, sufficient to replenish rinsing losses. After reaction, as shown in step 3, the excess dNTP solution 24 is forced back out through the frit 20 into the dNTP reservoir 24. In step 4 of the process the pipette is moved to a reservoir containing buffer solution and several aliquots of buffer solution are aspirated through the frit to rinse excess unbound dNTP from the beads. The buffer inside the pipette is then forced out and discarded to waste 26. The pipette is moved to a second buffer reservoir (buffer 2), containing the chemicals required to cleave the fluorescent tag from the incorporated dNMP. The reaction is allowed to occur to cleave the tag. As shown in step 5 the bead/buffer slurry with the detached fluorescent tag in solution is irradiated by a laser or light source 28 at a wavelength chosen to excite the fluorescent tag, the fluorescence is detected by fluorescence detector 30 and quantified if incorporation has occurred.

Subsequent steps depend on the enzyme strategy used. If a single-stage strategy with an exonuclease-deficient polymerase is used, as illustrated in FIG. 7(b), the solution containing the detached fluorescent tag is discarded to waste (step 6) which is expelled, followed by a further rinse step with buffer 1 (step 7) which is thereafter discarded (step 8) and the pipette is moved to a second reservoir containing a different dNTP (step 9) and the process repeats starting from step 3, cycling through all four dNTPs.

Figure 8A:
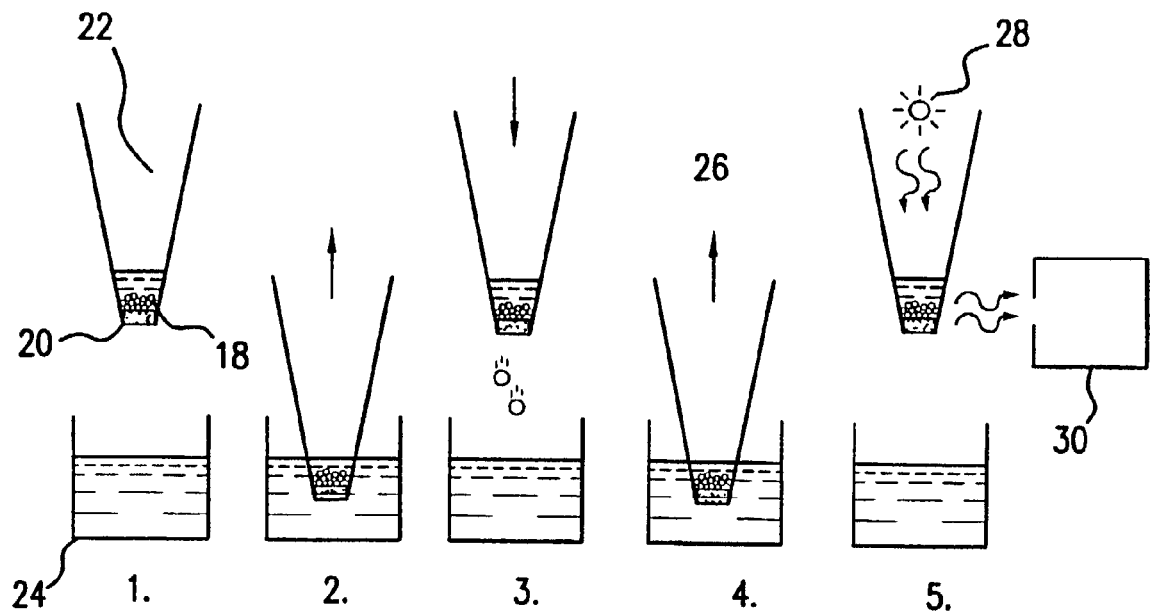
FIGS. 8(a) and 8(b) are schematic diagrams of a mechanical fluorescent sequencing method in accordance with the invention in which a DNA template and primer are absorbed on beads captured behind a porous frit.
Figure 8B:
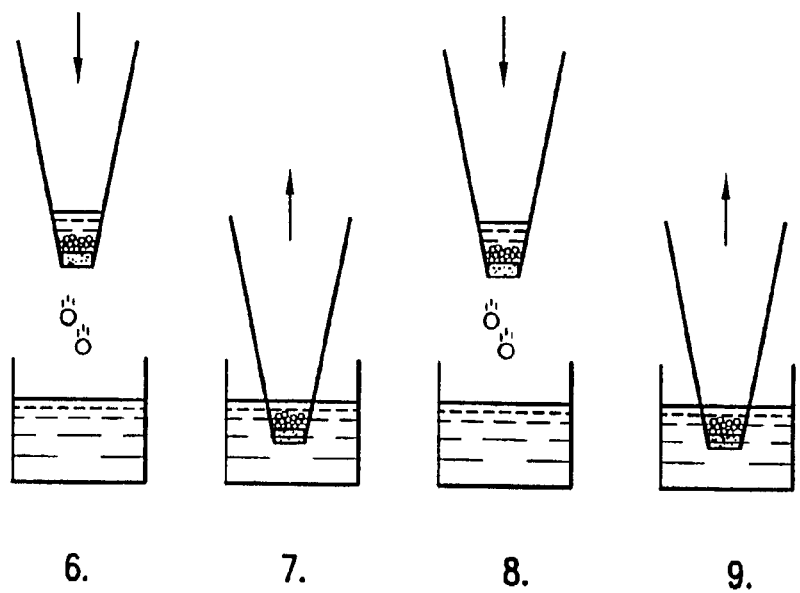
Figure 9:
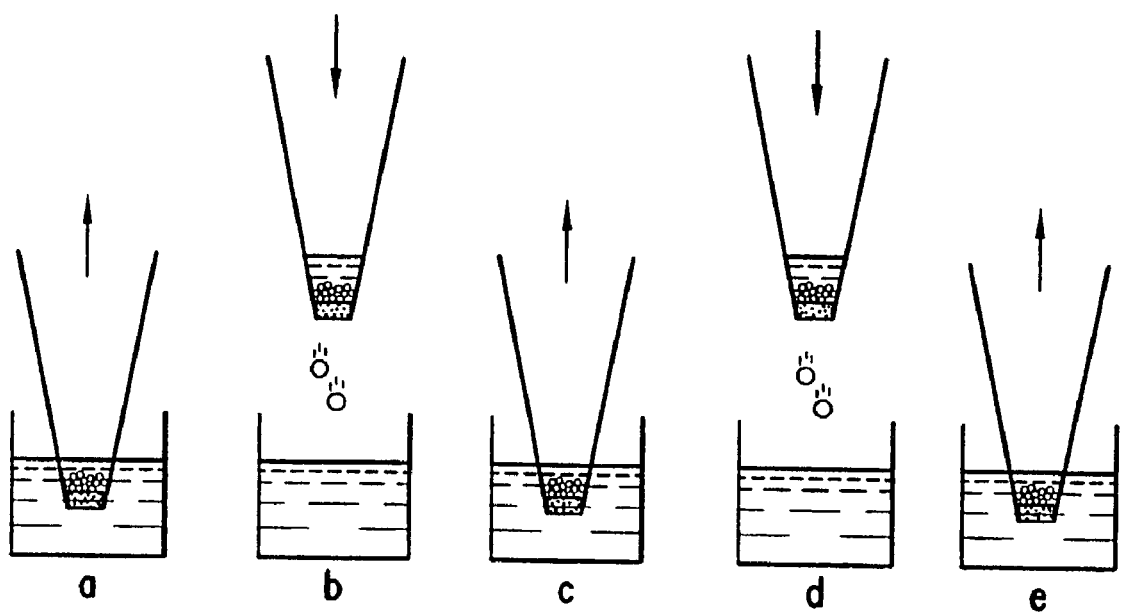
FIG. 9 is a schematic diagram of a sequencing method in accordance with the invention utilizing a two cycle system.

In a two-stage strategy, after the correct dNTP has been identified and the repeat length quantified in step 5, the reaction mixture is rinsed as shown in steps 6, 7, and 8 of FIG. 7(b) and the pipette is returned to a different reservoir containing the same dNTP (e.g., dNTP1) as shown in step (a) of FIG. 8 to which a quantity of exonuclease-proficient polymerase has been added and the solution is aspirated for a further stage of reaction which proof-reads the prior extension and correctly completes the extension. This second batch of dNTP need not be fluorescently tagged, as the identity of the dNTP is known and no sequence information will be gained in this proof-reading step. If a tagged dNTP is used, the fluorescent tag is preferably cleaved and discarded as in step 5 of FIG. 7(a) using Buffer 2. Alternatively, the initial incorporation reaction shown in step 2 of FIG. 7(a) is carried out for long enough, and the initial polymerase is accurate enough, so that the additional amount of fluorescent tag incorporated with dNTP1 at step a of FIG. 8 is small and does not interfere with quantification of the subsequent dNTP. Following proof-reading in step a of FIG. 8, excess dNTP is expelled (step b) and the reaction mixture is rinsed (steps c, d) with a high-salt buffer to dissociate the exo+ polymerase from the DNA primer/template. It is important not to have exonuclease-proficient enzyme present if the DNA primer/template is exposed to an incorrect dNTP. The pipette is then moved to step e, in which the reservoir contains a different dNTP, and the process is repeated, again cycling through all four dNTPs.

Although the invention has been described herein with reference to specific embodiments, many modifications and variations therein will readily occur to those skilled in the art. Accordingly, all such variations and modifications are included within the intended scope of the invention.

The invention claimed is:

1. A method of nucleic acid sequencing, the method comprising the steps of:
   (a) providing a nucleic acid template/primer system comprising individual template/primer duplexes immobilized on a surface;
   (b) exposing said individual template/primer duplexes to a polymerase and one or more type of nucleotide comprising an optically-detectable label, wherein said optically-detectable label is not attached to the 3' position of the sugar moiety of said nucleotide;
   (c) removing nucleotide that is not incorporated into a primer;
   (d) detecting incorporated nucleotide by the presence of said label;
   (e) removing said label from said incorporated nucleotide;
   (f) repeating steps (b) through (e) at least once with a different type of nucleotide comprising an optically-detectable label for incorporation into said primer; and
   (g) determining a nucleic acid sequence based upon said incorporated nucleotides.

2. The method of claim 1, wherein said label is a fluorescent label.

3. The method of claim 2, wherein said fluorescent label is selected from the group consisting of fluorescein, rhodamine and BODIPY.

4. The method of claim 2, wherein said detecting step comprises sensing said label.

5. The method of claim 1, wherein said detecting step comprises resolving an image of said duplex.

* * * * *

UNITED STATES PATENT AND TRADEMARK OFFICE
CERTIFICATE OF CORRECTION

PATENT NO. : 7,037,687 B2 Page 1 of 1
APPLICATION NO. : 10/229997
DATED : May 2, 2006
INVENTOR(S) : Peter Williams It is certified that error appears in the above-identified patent and that said Letters Patent is hereby corrected as shown below:

On Title Page, Item 75   Col. 1 under item (75) Inventors, the inventors
"Mark A. Hayes, Chandler, AZ (US); Seth D. Rose, Tempe, AZ (US); Linda B. Bloom, Chandler, AZ (US); Linda J. Reha-Krantz, Edmonton (CA); Vincent B. Pizziconi, Phoenix, AZ (US)"

should be changed to
-Tommy L. Ashton II, Chandler, AZ (US)-.

Signed and Sealed this

Twenty-ninth Day of August, 2006

JON W. DUDAS
*Director of the United States Patent and Trademark Office*

(12) INTER PARTES REEXAMINATION CERTIFICATE (467th)
United States Patent
Ashton, II

(10) Number: US 7,037,687 C1
(45) Certificate Issued: Oct. 5, 2012

(54) METHOD OF DETERMINING THE NUCLEOTIDE SEQUENCE OF OLIGONUCLEOTIDES AND DNA MOLECULES

(75) Inventor: Tommy L. Ashton, II, Chandler, AZ (US)

(73) Assignee: Arizona Board of Regents for and on Behalf of Arizona State University, Tempe, AZ (US)

Reexamination Request:
No. 95/001,532, Jan. 27, 2011

Reexamination Certificate for:
Patent No.: 7,037,687
Issued: May 2, 2006
Appl. No.: 10/229,997
Filed: Aug. 28, 2002

Certificate of Correction issued Aug. 29, 2006.

Related U.S. Application Data

(63) Continuation of application No. 09/673,544, filed as application No. PCT/US99/09616 on Apr. 30, 1999, now abandoned.

(60) Provisional application No. 60/083,840, filed on May 1, 1998.

(51) Int. Cl.
*C12P 19/34* (2006.01)
*C12Q 1/68* (2006.01)
*C07H 21/00* (2006.01)

(52) U.S. Cl. ......... 435/91.1; 435/91.2; 435/5; 435/6.12; 435/6.17; 536/22.1; 536/23.1

(58) Field of Classification Search ....................... None
See application file for complete search history.

(56) References Cited

To view the complete listing of prior art documents cited during the proceeding for Reexamination Control Number 95/001,532, please refer to the USPTO's public Patent Application Information Retrieval (PAIR) system under the Display References tab.

*Primary Examiner* — Padmashri Ponnaluri

(57) ABSTRACT

The present invention relates to a novel method for analyzing nucleic acid sequences based on real-time detection of DNA polymerase-catalyzed incorporation of each of the four nucleotide bases, supplied individually and serially in a microfluidic system, to a reaction cell containing a template system comprising a DNA fragment of unknown sequence and an oligonucleotide primer. Incorporation of a nucleotide base into the template system can be detected by any of a variety of methods including but not limited to fluorescence and chemiluminescence detection. Alternatively, microcalorimetic detection of the heat generated by the incorporation of a nucleotide into the extending template system using thermopile, thermistor and refractive index measurements can be used to detect extension reactions.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-5 are cancelled.

* * * * *